(12) United States Patent  (10) Patent No.: US 7,776,061 B2
Garner et al.  (45) Date of Patent: Aug. 17, 2010

(54) FLUID ADJUSTABLE BAND

(76) Inventors: Dean L. Garner, 5063 Lake Forest Dr., Cincinnati, OH (US) 45244; Randal T. Byrum, 1738 Westport Dr., Kings Mills, OH (US) 45034

( * ) Notice: Subject to any disclaimer, the term of this patent is extended or adjusted under 35 U.S.C. 154(b) by 570 days.

(21) Appl. No.: 10/952,209

(22) Filed: Sep. 28, 2004

(65) Prior Publication Data

US 2006/0074439 A1  Apr. 6, 2006

(51) Int. Cl.
*A61B 17/08* (2006.01)

(52) U.S. Cl. .................... 606/151; 606/157; 600/37

(58) Field of Classification Search ......... 606/151–158, 606/201, 202; 600/29–32, 37, 207
See application file for complete search history.

(56) References Cited

U.S. PATENT DOCUMENTS

| | | | |
|---|---|---|---|
| 3,745,998 A | | 7/1973 | Rose |
| 4,592,339 A | * | 6/1986 | Kuzmak et al. ............. 128/899 |
| 5,226,429 A | | 7/1993 | Kuzmak |
| 5,601,604 A | | 2/1997 | Vincent |
| 5,771,903 A | * | 6/1998 | Jakobsson ................... 128/898 |
| RE36,176 E | | 3/1999 | Kuzmak |
| 6,102,922 A | | 8/2000 | Jakobsson et al. |
| 6,453,907 B1 | | 9/2002 | Forsell |
| 6,461,292 B1 | | 10/2002 | Forsell |
| 6,470,892 B1 | | 10/2002 | Forsell |
| 6,607,542 B1 | * | 8/2003 | Wild .......................... 606/157 |
| 7,361,190 B2 | * | 4/2008 | Shaoulian et al. .......... 623/2.36 |
| 2003/0093117 A1 | * | 5/2003 | Saadat ........................ 606/221 |
| 2003/0105385 A1 | | 6/2003 | Forsell |
| 2003/0114729 A1 | | 6/2003 | Forsell |
| 2005/0251181 A1 | * | 11/2005 | Bachmann .................. 606/157 |
| 2005/0261713 A1 | * | 11/2005 | Hassan et al. ............... 606/157 |

FOREIGN PATENT DOCUMENTS

| | | |
|---|---|---|
| EP | 1396243 | 3/2004 |
| EP | 1645249 | 4/2006 |
| EP | 05255995 | 6/2006 |
| FR | 2846877 A1 | 5/2004 |
| WO | WO 03/059215 | 7/2003 |
| WO | WO 2004/010910 A1 | 2/2004 |

* cited by examiner

*Primary Examiner*—Darwin P Erezo
*Assistant Examiner*—Melanie Tyson

(57) ABSTRACT

A surgically implantable fluid adjustable device, such as an adjustable gastric band, having an elongated substantially flexible inflatable portion, and an elongated flexible and substantially inextensible band portion attached to the inflatable portion. The device further includes a member for changing the shape of the device from a straight configuration to a curved configuration after being implanted within a body.

3 Claims, 4 Drawing Sheets

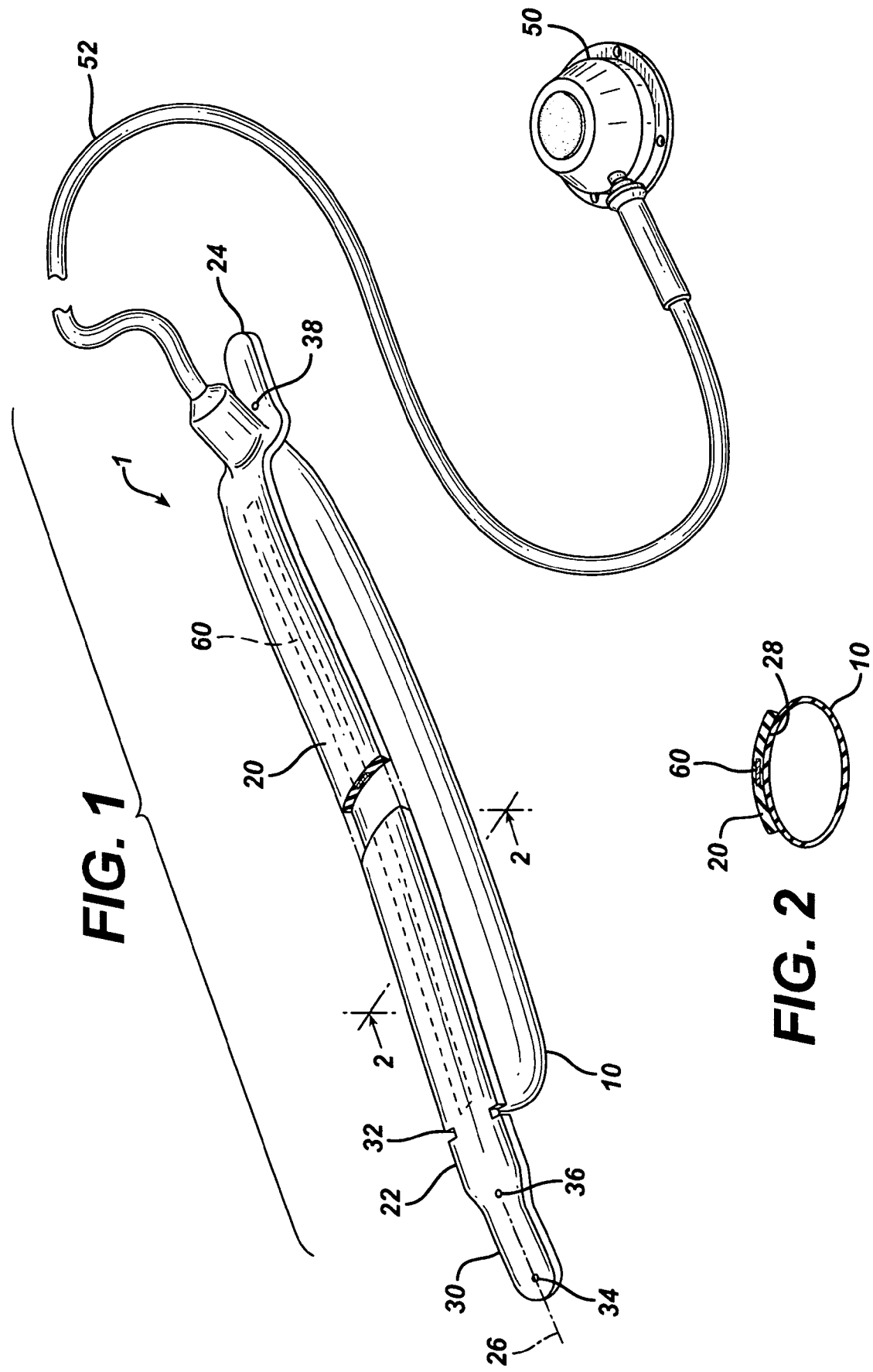

FLUID ADJUSTABLE BAND

FIELD OF THE INVENTION

The present invention has application in conventional endoscopic and open surgical instrumentation as well as application in robotic-assisted surgery. The present invention has even further relation to adjustable surgically implantable bands, such as gastric bands for the treatment of obesity.

BACKGROUND OF THE INVENTION

The percentage of the world's population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and failed to correct the condition. Mechanical apparatuses for insertion into the body through non-surgical means, such as the use of gastric balloons to fill the stomach have also been employed in the treatment of the condition. Such devices cannot be employed over a long term, however, as they often cause severe irritation, necessitating their periodic removal and hence interruption of treatment. Thus, the medical community has evolved surgical approaches for treatment of morbid obesity.

Most surgical procedures for treatment of morbid obesity may generally be classified as either being directed toward the prevention of absorption of food (malabsorption), or restriction of stomach to make the patient feel full (gastric restriction) The most common malabsorption and gastric restriction technique is the gastric bypass. In variations of this technique, the stomach is horizontally divided into two isolated pouches, with the upper pouch having a small food capacity. The upper pouch is connected to the small intestine, or jejunum, through a small stoma, which restricts the processing of food by the greatly reduced useable stomach. Since food bypass much of the intestines, the amount of absorption of food is greatly reduced.

There are many disadvantages to the above procedure. Typically the above mentioned procedure is performed in an open surgical environment. Current minimally invasive techniques are difficult for surgeons to master, and have many additional drawbacks. Also, there is a high level of patient uneasiness with the idea of such a drastic procedure which is not easily reversible. In addition, all malabsorption techniques carry ongoing risks and side effects to the patient, including malnutrition and dumping syndrome.

Consequently, many patients and physicians prefer to undergo a gastric restriction procedure for the treatment of morbid obesity. One of the most common procedures involves the implantation of an adjustable gastric band. In accordance with current practice, a gastric band is operatively placed to encircle the stomach. This divides the stomach into two parts with a stoma in-between. An upper portion, or a pouch, which is relatively small, and a lower portion which is relatively large. The small partitioned portion of the stomach effectively becomes the patient's new stomach, requiring very little food to make the patient feel full.

Once positioned around the stomach, the ends of the gastric band are fastened to one another and the band is held securely in place by folding a portion of the gastric wall over the band and closing the folded tissue with sutures placed therethrough thereby preventing the band from slipping and the encircled stoma from expanding.

During the placement of gastric bands, the device must be inserted into the body through a trocar, placed around the stomach, and locked in place. Physical properties and geometry of the band contribute to making some of these steps easier than others. For example, a soft, flaccid band would be easy to place through a trocar and be atraumatic to tissue, but be more difficult to orient around the stomach. A more rigid, pre-curved band would be easy to place around the stomach, but be more difficult to place through a trocar and be more traumatic to tissue. This present invention solves this problem by providing a band which would be capable of having multiple configurations wherein it could have soft, flaccid features at one moment, and more curved, rigid properties at another. This could be accomplished in a number of ways.

SUMMARY OF THE INVENTION

In accordance with the present invention, there is provided a surgically implantable fluid adjustable device, such as an adjustable gastric band, having an elongated substantially flexible inflatable portion, and an elongated flexible and substantially inextensible band portion attached to the inflatable portion. The device further includes a member for changing the shape of the device from a straight configuration to a curved configuration after being implanted within a body.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 1 is a perspective view of an surgically implantable fluid adjustable device 1 made in accordance with the present invention.

FIG. 2 is a cross section of the device shown in FIG. 1, taken along lines 2-2.

DETAILED DESCRIPTION OF THE INVENTION

Figure 3:
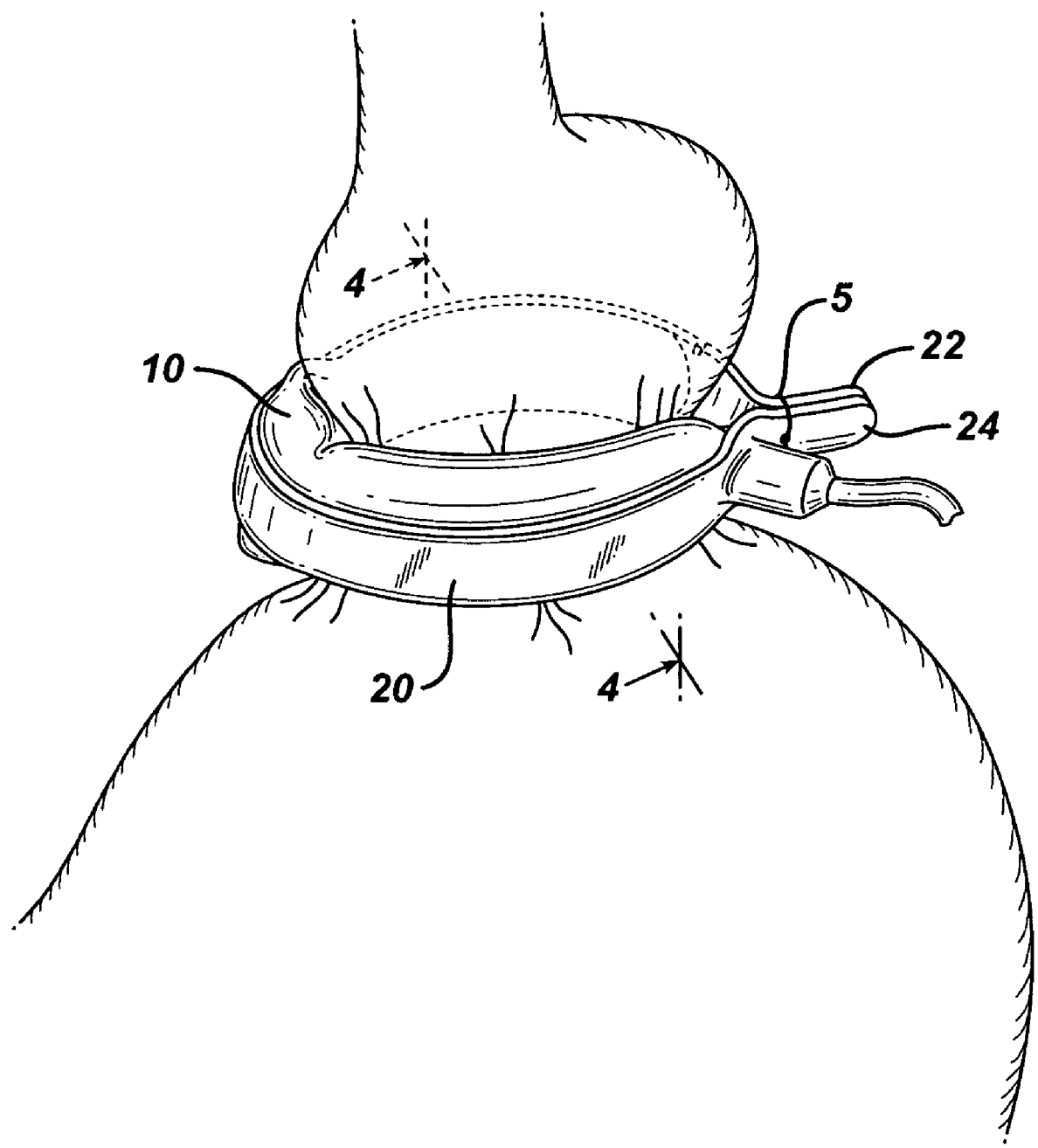
FIG. 3 is a perspective view of a device 1 implanted into a body of a patient.
Figure 4:
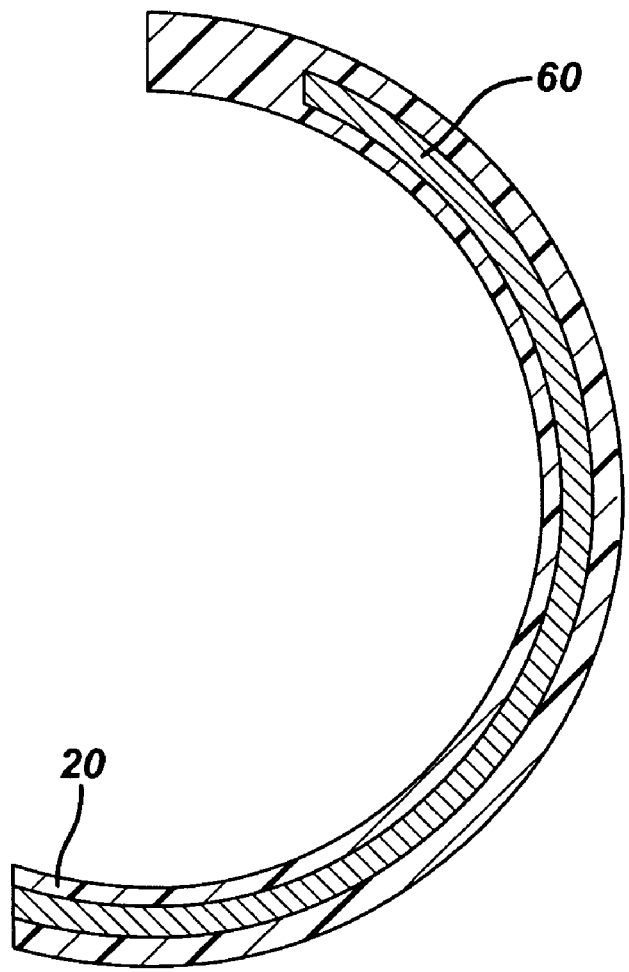
FIG. 4 is a simplified cross section of inextensible portion 20 of device 1.

Referring now to FIG. 1, there is shown a surgically implantable device 1 made in accordance with the present invention. Device 1 is similar to the devices described in U.S. Pat. Nos. 4,592,339 issued to Kuzmak; RE 36176 issued to Kuzmak; 5,226,429 issued to Kuzmak; 6,102,922 issued to Jacobson and 5,601,604 issued to Vincent, all of which are hereby incorporated herein by reference. The device includes an elongated flexible inflatable balloon portion 10. Balloon portion 10 is substantially evacuated of fluids prior to the devices implantation in a patient. Balloon portion 10 can be made from any number of materials known to those skilled in the art including silicone and polyurethane. In addition, such bands can be coated with materials to improve the prevention of diffusion. Such coatings include titanium powder and are described in PCT patent application WO 2004/010910 A1 which is hereby incorporated herein by reference.

Device 1 further includes and an elongated flexible and substantially inextensible band portion 20. The band portion has a distal end 22, a proximal end 24 and a longitudinal axis 26 therebetween. Band portion 20 can be made from any number of materials known to those skilled in the art including silicone and polyurethane. The band portion is attached to the balloon portion along an inner face 28 of the band portion 20. The inflatable or balloon portion 10 can be attached to band portion 20 by any number of means known to those skilled in the art including using a silicone adhesive. The two portions may also be integrally manufactured as one part.

The distal and proximal ends of the band portions include means for attaching such ends together. There are various means for attaching the distal and proximal ends of the band together. Many of these are described in co-pending and commonly assigned U.S. patent application Ser. No. 60/483,353 filed Sep. 30, 2003, 60/507,916 filed Sep. 30, 2003 and 60/507,625 filed Sep. 30, 2003 the disclosures of which are hereby incorporated herein by reference. FIG. 1 shows the distal end of the band 22 as comprising a tab 30 having notches 32. This tab 30 would be inserted into a slot (not shown) on the proximal end 24 of band 20. Tab 30 also includes suture holes 34 and 36, one of which would line up with suture hole 38 on the proximal end 24 of band 20. After the tab 30 is inserted into the slot, and the physician is pleased with the final position of the band, the ends 22 and 24 are then often sutured together to better secure the band in position. However, many alternative locking means, such as those described in the above incorporated reference, do not need to use suture.

Inflatable portion 10 is shown as being in fluid communication with an injection port 50 via a catheter tube 52. However, inflatable portion 10 could also be fluidly connected to an implanted reservoir such as those used with remotely controlled bands. Such a band is described in U.S. Pat. No. 6,453,907 issued on Sep. 24, 2002, which is hereby incorporated herein by reference. Port 50 is of the type well known in the medical field not only for gastric bands, but such ports are also used for vascular access for drug delivery. After device 1 is implanted into a patient, port 50 is attached just below the skin of the patient, so that fluid can be inserted and withdrawn from the inflatable portion with a syringe. Catheter tube 52 can be integral with inflatable portion 10 or can be a separate piece.

Figure 5:
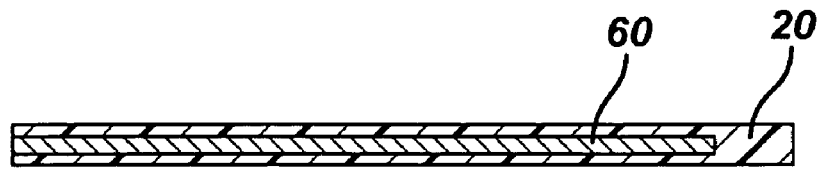
FIG. 5 is a view similar to that shown in FIG. 4 but showing portion 20 in its straight configuration.
Figure 6:
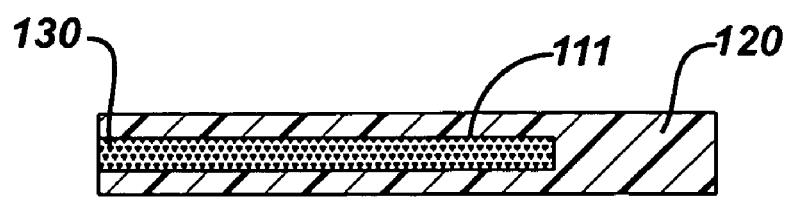
FIG. 6 is a view similar to that shown in FIG. 5 but showing an alternative embodiment.

Device 1 further includes a means or member for changing the shape the device from a straight configuration, shown in FIG. 1, to a curved configuration, shown in FIG. 2, after being implanted within a body. By referring to FIGS. 1, 2, 4 and 5 one embodiment for this member is a strip of shape memory alloy 60 disposed along the length of the device. Strip 60 has a straight shape below body temperature (FIG. 5), and a curved shape at body temperature (FIG. 6). The strip should have sufficient shape recovery force to curve the device upon being implanted within a body.

One type of shape memory material is commonly referred to as Nitinol. The nature of this material is discussed in "Engineering Aspects of Shape Memory Alloys", T W Duerig et al. Butterworth-Heinemann (1990). A principal characteristic of shape memory alloys involves an initial increase in strain, approximately linearly with stress. This behavior is reversible, and corresponds to conventional elastic deformation. Subsequent increases in strain are accompanied by little or no increase in stress, over a limited range of strain to the end of the "loading plateau". Nitinol or Ni—Ti binary alloys have a nickel content of at least about 50 atomic percent (hereinafter at. %), preferably at least about 50.5 at. %. The nickel content will usually be less than about 54 at. %, preferably less than about 52 at. %. For strip 60 to have a straight shape outside of the body, and to curve when raised to body temperature it should have an Austenitic Start Temperature (As) below body temperature (37° C.) but above operating room temperature (16° C. to 20° C., preferably above 18° C.), and an Austenitic Finish Temperature (Af) of at least body temperature (37° C.).

The figures show strip 60 as being embedded with portion 20. However, it could be places in the inflatable portion 10 as well. Member 60 could be permanently attached, or could be removable. For example member 60 could sit in a pocket on portion 12 and could be removed through an opening or the like. Member 60 can be integral with at least one of the inflatable portion and the band portion.

Figure 7:
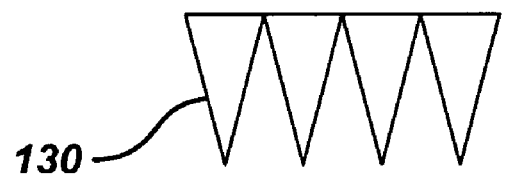
FIG. 7 is a partial simplified flat view of the triangular media 130 shown in FIG. 6.
Figure 8:
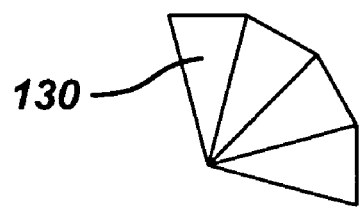
FIG. 8 is a view similar to that of FIG. 7 but showing media 130 in their curved configuration.

An alternative embodiment of the means or member for changing the shape the device from a straight configuration to a curved configuration is shown in FIGS. 6-8. In this embodiment a non extensible portion 120, similar to that of portion 20, but having an elongated cavity 111 disposed therein. Portion 120 has a connection allowing a vacuum to be applied to 111. Cavity 111 has a plurality of media disposed therein. Media 130 are shown as triangular shaped plastic pellets, but could be made from any number of materials and shapes known to those skilled in the art. The media 130 could also be connected to each other and hinged at the connection points. When vacuum is applied to cavity 111 the individual media come into close contact and take on the shape shown in FIG. 8. This would cause the entire portion 120 to take on a caved configuration. Therefore, the band would be placed into the body without vacuum being applied so that it is in a straight configuration. Once inside the body, vacuum can then be applied to that the band takes on a curved configuration. After implanted, the vacuum could then be removed so that the band is softer and less rigid while in the body.

When implanting the band the physician would prepare the patient and the surgical site therein according to normal well known surgical procedures. Such known surgical procedures typically involve placing the device 1 down a trocar, such as the Xcel and EndoPath trocars sold by Ethicon Endo-Surgery, Inc., Cincinnati Ohio. For the physician, it is easier to insert the band down the trocar when it is in a straight configuration. However, then the physician must place the band around a retrogastric tunnel posterior to the stomach. This is more easily accomplished by having the device 1 in the curved configuration. The band is then grasped on the plug and pulled posteriorly through the retrogastric tunnel and then be placed around the organ, as shown in FIG. 3, and secured with a suture 5 or the like It will become readily apparent to those skilled in the art that the above invention is has equal applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

While embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. A surgically implantable fluid adjustable solid device comprising:
 a. an elongated substantially flexible inflatable portion; and
 b. an elongated flexible and substantially inextensible band portion attached to said inflatable portion; and
 c. said device having two unrestrained shapes depending on a temperature of said device, a straight configuration to a curved configuration, and a temperature activated member which changes the shape of said device from said straight configuration to said curved configuration, while remaining solid, after its temperature is raised, said member comprising a strip of shape memory alloy disposed along the length of the device, said strip having a straight shape substantially along its entire length below body temperature, and a single curved shape at body temperature, wherein the strip has sufficient shape recovery force to curve said device into said single curved shape upon being implanted within a body without the application of an external heat source, and wherein said strip has an Af temperature of at least 37° C. and an As temperature greater than 18° C. and less than 37° C., said member being embedded within said elongated flexible and substantially inextensible band portion.

2. The device of claim 1 wherein said member which changes the shape of said device is integral with said elongated flexible and substantially inextensible band portion.

3. The device of claim 1 wherein said shape memory comprises Nitinol.

\* \* \* \* \*